United States Patent
Yamazaki

(10) Patent No.: US 11,330,971 B2
(45) Date of Patent: May 17, 2022

(54) ENDOSCOPE SYSTEM AND PROCESSOR WITH LIGHT ADJUSTMENT CONTROL

(71) Applicant: OLYMPUS CORPORATION, Toyko (JP)

(72) Inventor: Ryuichi Yamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 351 days.

(21) Appl. No.: 16/715,435

(22) Filed: Dec. 16, 2019

(65) Prior Publication Data

US 2020/0113423 A1 Apr. 16, 2020

Related U.S. Application Data

(63) Continuation of application No. PCT/JP2018/018808, filed on May 15, 2018.

(30) Foreign Application Priority Data

Jun. 21, 2017 (JP) .............................. JP2017-121520

(51) Int. Cl.
*A61B 1/045* (2006.01)
*A61B 1/06* (2006.01)
(Continued)

(52) U.S. Cl.
CPC ............ *A61B 1/045* (2013.01); *A61B 1/0646* (2013.01); *A61B 1/0676* (2013.01); *G02B 23/24* (2013.01);
(Continued)

(58) Field of Classification Search
None
See application file for complete search history.

(56) References Cited

U.S. PATENT DOCUMENTS

2003/0076411 A1* 4/2003 Iida ..................... H04N 7/183
348/65
2011/0034770 A1 2/2011 Endo et al.

FOREIGN PATENT DOCUMENTS

JP H11-76157 A 3/1999
JP 2003-180631 A 7/2003
(Continued)

OTHER PUBLICATIONS

International Search Report dated Aug. 14, 2018 received in PCT/JP2018/018808.

*Primary Examiner* — John P Leubecker
(74) *Attorney, Agent, or Firm* — Scully, Scott, Murphy & Presser, P.C.

(57) ABSTRACT

An endoscope system, wherein a processor reads out light distribution information which is information indicating a relationship between an arrangement of an image pickup device and a distribution of illumination light emission positions and which includes information about a light distribution angle of illumination light and the number of illuminating portions, a part of parameters of a light adjustment parameter and a parameter flag from an endoscope, and controls amounts of light of the illuminating portions by selecting the part of the parameters with priority over the light adjustment parameters at time of selecting the light adjustment parameter based on the light distribution information, if it is specified by the parameter flag that the part of the parameters are used for the light adjustment.

8 Claims, 12 Drawing Sheets

(51) Int. Cl.
 *G02B 23/24* (2006.01)
 *A61B 1/00* (2006.01)
(52) U.S. Cl.
 CPC ......... *A61B 1/00006* (2013.01); *A61B 1/0661* (2013.01)

(56) References Cited

FOREIGN PATENT DOCUMENTS

| | | |
|---|---|---|
| JP | 2011-036361 A | 2/2011 |
| JP | 2013-000175 A | 1/2013 |

\* cited by examiner

FIG. 5

| IMAGER | THE NUMBER OF LG'S | EXTENSION BIT | LAYOUT | LIGHT ADJUSTMENT PARAMETER | CHARACTERISTIC OF LIGHT ADJUSTMENT CONTROL |
|---|---|---|---|---|---|
| Ty1 | 1 | 0 | A LAYOUT | a | SUPPRESS HALATION IN UPPER PART |
|  | 3 | 0 | D LAYOUT | c | CONTROL ACCORDING TO LUMINANCE VALUE IN CENTER OF SCREEN |
|  | 2 | 1 | E LAYOUT | b' | SUPPRESS HALATION IN LOWER PART |
| Ty2 | 2 | 0 | B LAYOUT | b | CONTROL ACCORDING TO LUMINANCE VALUE IN CENTER OF SCREEN |
|  | 3 | 0 | D LAYOUT | c | CONTROL ACCORDING TO LUMINANCE VALUE IN CENTER OF SCREEN |
|  | 1 | 0 | A LAYOUT | a | SUPPRESS HALATION IN UPPER PART |
| Ty3 | 2 | 0 | C LAYOUT | b | CONTROL ACCORDING TO LUMINANCE VALUE IN CENTER OF SCREEN |
|  | 2 | 1 | E LAYOUT | b' | SUPPRESS HALATION IN LOWER PART |
|  | 1 | 0 | A LAYOUT | a | SUPPRESS HALATION IN UPPER PART |
| Ty4 | 3 | 0 | D LAYOUT | c | CONTROL ACCORDING TO LUMINANCE VALUE IN CENTER OF SCREEN |
|  | 2 | 1 | E LAYOUT | b' | SUPPRESS HALATION IN LOWER PART |

FIG. 10

| OBSERVATION SITE | THE NUMBER OF LG'S | EXTENSION BIT | LAYOUT | LIGHT ADJUSTMENT PARAMETER |
|---|---|---|---|---|
| BRONCHUS | 1 | 0 | A LAYOUT | P1 |
| | 2 | 0 | B LAYOUT | P2 |
| UPPER DIGESTIVE TRACT | 2 | 0 | C LAYOUT | P3 |
| | | 1 | E LAYOUT | P4 |
| | 3 | 0 | D LAYOUT | P5 |
| LOWER DIGESTIVE TRACT | 2 | 0 | C LAYOUT | P6 |
| | | 1 | E LAYOUT | P7 |
| | 3 | 0 | D LAYOUT | P8 |
| TRANSNASALLY OBSERVED SITE | 2 | 0 | C LAYOUT | P9 |

ENDOSCOPE SYSTEM AND PROCESSOR WITH LIGHT ADJUSTMENT CONTROL

CROSS REFERENCE TO RELATED APPLICATION

This application is a continuation application of PCT/JP2018/018808 filed on May 15, 2018 and claims benefit of Japanese Application No. 2017-121520 filed in Japan on Jun. 21, 2017, the entire contents of which are incorporated herein by this reference.

BACKGROUND OF THE INVENTION

1. Field of the Invention

The present invention relates to an endoscope system for observing a subject using an endoscope, and a processor.

2. Description of the Related Art

Recently, endoscopes have been used in various fields, for example, a medical field and an industrial field. For example, endoscopes in the medical field are used for observation of an organ in a body cavity, treatment using a treatment instrument, a surgical operation under endoscopic observation, and the like.

As such endoscopes, there are some that are provided with an image pickup portion configured to pick up an image of an inside of a subject. An optical image from the subject is formed on an image pickup surface of an image pickup device constituting the image pickup portion via an optical system provided in an insertion portion. The image pickup device is adapted to photoelectrically convert the incident optical image to obtain an image pickup signal.

By the way, an endoscope configured to observe an inside of a living body requires a light source device configured to illuminate a subject. Illumination light generated by the light source device is radiated to an observation target subject from a distal end portion where the image pickup portion exists, via a light guide inserted in the insertion portion of the endoscope. An amount of the illumination light is automatically adjusted based on brightness of an endoscopic image generated based on an image pickup signal.

For example, Japanese Patent Application Laid-Open Publication No. 2003-180631 discloses a technique in which an endoscopic image is divided into a plurality of areas, and brightness adjustment is performed, with an overall luminance value determined using a weighting factor set for each of the areas as brightness of the endoscopic image. In this case, in a proposal of Japanese Patent Application Laid-Open Publication No. 2003-180631, a technique of determining the weighting factor to be set for each of the area based on data of an arrangement relationship between an objective lens and a light distribution lens on a distal end portion of a video scope.

Note that a position in an endoscopic image on a screen that a surgeon wants to observe may differ according to an observation site or according to difference between near-point observation and far-point observation and the like.

SUMMARY OF THE INVENTION

An endoscope system of an aspect of the present invention is an endoscope system including an endoscope including an image pickup device configured to pick up an image of an inside of a subject and one or more illuminating portions configured to emit illumination light, and a processor, the endoscope system selecting a light adjustment parameter used for light adjustment control of the illuminating portions from among a plurality of light adjustment parameters each of which includes one or more parameters about light adjustment, based on light distribution information which is information indicating a relationship between an arrangement of the image pickup device and a distribution of illumination light emission positions corresponding to positions of the illuminating portions and which includes information about a light distribution angle of the illumination light and a number of the illuminating portions, to perform light adjustment control, wherein the endoscope includes an endoscope memory configured to store the light distribution information, a part of parameters of the light adjustment parameter, and a parameter flag specifying that the part of the parameters are used for the light adjustment; the processor includes a memory configured to store the plurality of light adjustment parameters corresponding to pieces of the light distribution information according to a plurality of types of endoscopes; and the processor reads out the light distribution information, the part of the parameters, and the parameter flag from the endoscope memory, and controls amounts of light of the illuminating portions by selecting the part of the parameters with priority over the light adjustment parameters stored in the memory at time of selecting the light adjustment parameter based on the light distribution information, if it is specified by the parameter flag that the part of the parameters are used for the light adjustment.

A processor according to an aspect of the present invention is a processor connectable to an endoscope including an image pickup device configured to pick up an image of an inside of a subject and one or more illuminating portions configured to emit illumination light, the processor selecting a light adjustment parameter used for light adjustment control of the illuminating portions from among a plurality of light adjustment parameters each of which includes one or more parameters about light adjustment, based on light distribution information which is information indicating a relationship between an arrangement of the image pickup device and a distribution of illumination light emission positions corresponding to positions of the illuminating portions and which includes information about a light distribution angle of the illumination light and a number of the illuminating portions, to perform light adjustment control, wherein the processor includes a memory configured to store the plurality of light adjustment parameters corresponding to pieces of the light distribution information according to a plurality of types of endoscopes; and the processor reads out the light distribution information, a part of the parameters, and a parameter flag specifying that the part of the parameters are used for the light adjustment that are stored in the endoscope that is connected, and controls amounts of light of the illuminating portions by selecting the part of the parameters with priority over the light adjustment parameters stored in the memory at time of selecting the light adjustment parameter based on the light distribution information, if it is specified by the parameter flag that the part of the parameters are used for the light adjustment.

BRIEF DESCRIPTION OF THE DRAWINGS

FIG. 5 is an explanatory diagram for illustrating an example of a light adjustment parameter table stored in a memory 25;

FIG. 10 is an explanatory diagram for illustrating a modification;

DETAILED DESCRIPTION OF THE PREFERRED EMBODIMENT(S)

Embodiments of the present invention will be described below in detail with reference to drawings.

First Embodiment

Figure 1:
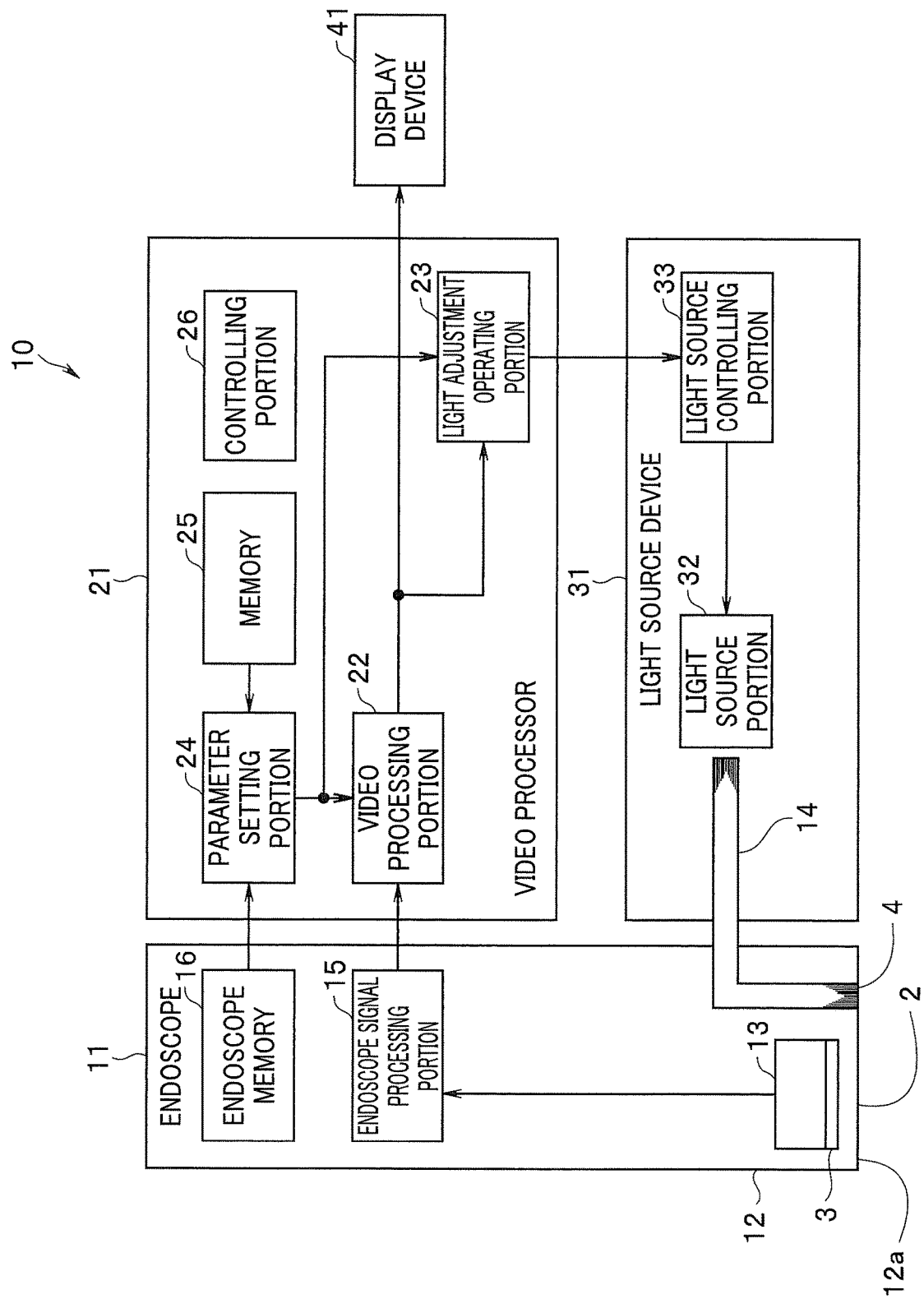
FIG. 1 is a block diagram showing an endoscope system according to a first embodiment of the present invention.

FIG. 1 is a block diagram showing an endoscope system according to a first embodiment of the present invention.

In the present embodiment, light distribution information indicating a relationship between an arrangement of an image pickup device and a distribution of illumination light emission positions is stored in an endoscope memory. The light distribution information may be, for example, angles of the illumination light emission positions relative to an arrangement position of the image pickup device (light distribution angles), the number of the illumination light emission positions, and information about bias of the illumination light emission positions. If a pattern of the distribution of the illumination light emission positions for the arrangement of the image pickup device is specified, information showing the pattern may be stored in the endoscope memory. In the present embodiment, light adjustment control for controlling brightness of a part to be observed to be proper brightness is performed by setting a light adjustment parameter used for the light adjustment control based on the light distribution information read out from the endoscope memory.

First, description will be made on brightness of a screen according to a relationship between the arrangement of the image pickup device and the distribution of the illumination light emission positions with reference to FIGS. 2A to 2E and FIG. 3. FIGS. 2A to 2E are explanatory diagrams showing examples of an arrangement relationship of an illumination window/illumination windows relative to the image pickup device corresponding to an objective lens on a distal end face of a distal end of an endoscope insertion portion. Note that, in the description below, a distal end layout shows the distribution of the illumination light emission positions (positions of the illumination windows) relative to the arrangement of the image pickup device.

Figure 2A:
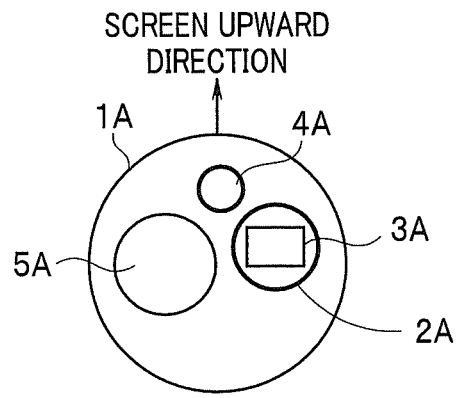
FIG. 2A is an explanatory diagram showing an example of an arrangement relationship of an illumination window relative to an image pickup device corresponding to an objective lens on a distal end face of a distal end of an endoscope insertion portion.

FIG. 2A shows a distal end layout of an insertion portion 1A (hereinafter referred to as an A layout). As for the insertion portion 1A in FIG. 2A, an observation window (an objective lens) 2A is arranged on a right end side near a center of a distal end face in a vertical direction, and an image pickup device 3A is disposed in an inside of the insertion portion 1A facing the observation window 2A. The image pickup device 3A is arranged such that a screen upward direction of a picked-up image (an endoscopic image) obtained by being picked up by the image pickup device 3A corresponds to a screen upward direction shown by an arrow in FIG. 2A. Note that, in each of FIGS. 2B to 2E described later, an arrangement is made such that a screen upward direction of a picked-up image (an endoscopic image) obtained by being picked up by a built-in image pickup device corresponds to a screen upward direction shown by an arrow in each figure, and the vertical direction on a distal end face of each insertion portion is based on the screen upward direction.

On an upper part of a center of the distal end face in a horizontal direction, an illumination window 4A, which is an illumination light emission surface, is disposed. That is, the A layout of FIG. 2A shows an example in which the illumination window 4A composing an illuminating portion is arranged in a diagonally upward direction from the image pickup device 3A. Note that, on a left end from the center of the distal end face in the vertical direction, a treatment instrument channel 5A is provided.

Figure 2B:
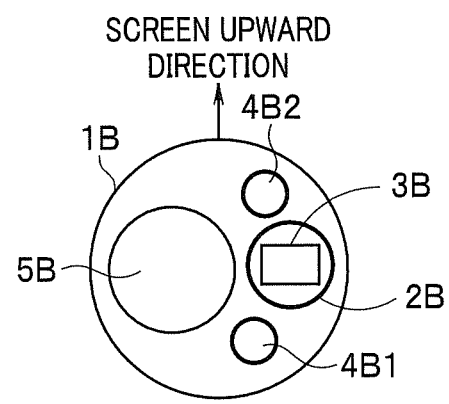
FIG. 2B is an explanatory diagram showing an example of an arrangement relationship of illumination windows relative to an image pickup device corresponding to an objective lens on a distal end face of a distal end of an endoscope insertion portion.

FIG. 2B shows a distal end layout of an insertion portion 1B (hereinafter referred to as a B layout). As for the insertion portion 1B in FIG. 2B, an observation window (an objective lens) 2B is arranged on a right end side of a center of a distal end face in the vertical direction, and an image pickup device 3B is disposed in an inside of the insertion portion 1B facing the observation window 2B. In downward and upward directions of and relatively near the image pickup device 3B, illumination windows 4B1 and 4B2, each of which is an illumination light emission surface, are disposed. That is, the B layout of FIG. 2B shows an example in which the illumination windows 4B1 and 4B2 are arranged on both sides of the image pickup device 3B in the vertical direction. Note that, on a left end from the center of the distal end face in the vertical direction, a treatment instrument channel 5B is provided.

Figure 2C:
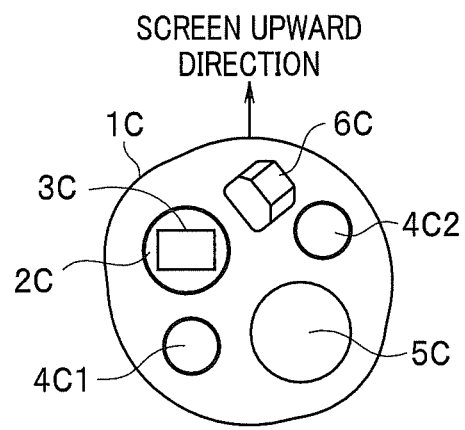
FIG. 2C is an explanatory diagram showing an example of an arrangement relationship of illumination windows relative to an image pickup device corresponding to an objective lens on a distal end face of a distal end of an endoscope insertion portion.

FIG. 2C shows a distal end layout of an insertion portion 1C (hereinafter referred to as a C layout). As for the insertion portion 1C in FIG. 2C, an observation window (an objective lens) 2C is arranged in a slightly upper left of a center of a distal end face in the vertical direction, and an image pickup device 3C is disposed in an inside of the insertion portion 1C facing the observation window 2C. Below the image pickup device 3C, an illumination window 4C1, which is an illumination light emission surface, is disposed. In a slightly upward direction on a right side of the image pickup device 3C, an illumination window 4C2, which is an illumination light emission surface, is disposed.

The C layout of FIG. 2C shows an example in which the illumination windows 4C1 and 4C2 are arranged above and below the image pickup device 3C in the vertical direction. Note that a treatment instrument channel 5C is provided at a position in a diagonally lower right direction from the center of the distal end face, and a water feeding nozzle 6C is disposed near an upper end from the center of the distal end face in the horizontal direction.

Figure 2D:
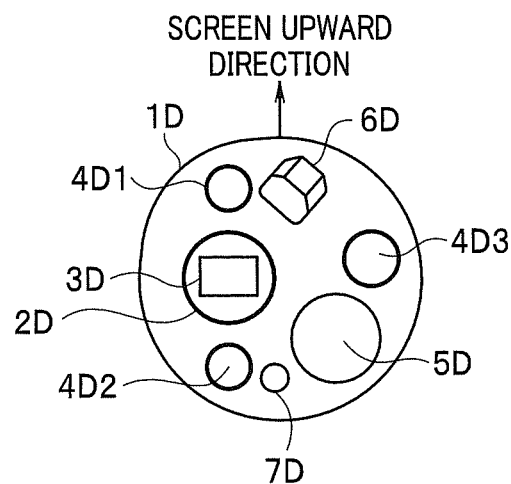
FIG. 2D is an explanatory diagram showing an example of an arrangement relationship of illumination windows relative to an image pickup device corresponding to an objective lens on a distal end face of a distal end of an endoscope insertion portion.

FIG. 2D shows a distal end layout of an insertion portion 1D (hereinafter referred to as a D layout). As for the insertion portion 1D in FIG. 2D, an observation window (an objective lens) 2D is arranged on a slightly left side of a center of a distal end face in the vertical direction, and an image pickup device 3D is disposed in an inside of the insertion portion 1D facing the observation window 2D. Above the image pickup device 3D, an illumination window 4D1, which is an illumination light emission surface, is disposed. Below the image pickup device 3D, an illumination window 4D2, which is an illumination light emission surface, is disposed. In a slightly upward direction on a right side of the image pickup device 3D, an illumination window 4D3, which is an illumination light emission surface, is disposed.

The D layout of FIG. 2D shows an example in which the three illumination windows 4D1 to 4D3 are almost evenly arranged above and below the image pickup device 3D in the vertical direction. Note that a treatment instrument channel 5D is provided at a position in a diagonally lower right direction from a center of the distal end face, and a water feeding nozzle 6D is disposed near an upper end from the center of the distal end face in the horizontal direction. Further, near a lower end from the center of the distal end face in the horizontal direction, a secondary water feeding opening 7D is disposed.

Figure 2E:
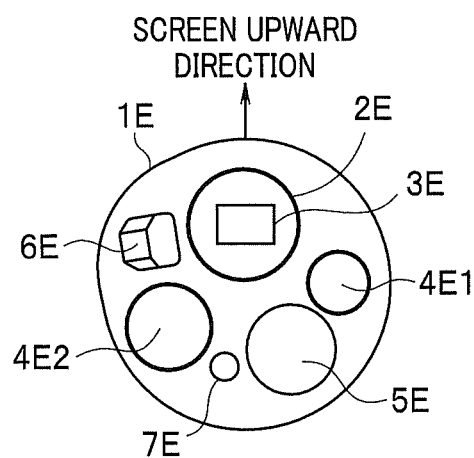
FIG. 2E is an explanatory diagram showing an example of an arrangement relationship of illumination windows relative to an image pickup device corresponding to an objective lens on a distal end face of a distal end of an endoscope insertion portion.

FIG. 2E shows a distal end layout of an insertion portion 1E (hereinafter referred to as an E layout). As for the insertion portion 1E in FIG. 2E, an observation window (an objective lens) 2E is arranged above a center of a distal end face in the horizontal direction, and an image pickup device 3E is disposed in an inside of the insertion portion 1E facing the observation window 2E. In a downward direction on a right side of the image pickup device 3E, an illumination window 4E1, which is an illumination light emission surface, is disposed. On a left side below the image pickup device 3D, an illumination window 4E2, which is an illumination light emission surface, is disposed.

The E layout of FIG. 2E shows an example in which the illumination windows 4E1 and 4E2 are arranged being biased on a lower side of the image pickup device 3E in the vertical direction. Note that a treatment instrument channel 5E is provided at a position in a diagonally lower right direction from a center of a distal end face, and a water feeding nozzle 6E is disposed on an end portion in a diagonally upper left direction from a center of the distal end face. Further, near a lower end from the center of the distal end face in the horizontal direction, a secondary water feeding opening 7E is disposed.

Note that, in the description below, the observation windows 2A to 2E will be referred to as an observation window 2 when the observation windows 2A to 2E are not mutually distinguished; the image pickup devices 3A to 3E will be referred to as an image pickup device 3 when the image pickup devices 3A to 3E are not mutually distinguished; and the illumination windows 4A, 4B1, 4B2, 4C1, 4C2, 4D1 to 4D3, 4E1, 4E2 will be referred to as an illumination window 4 when the illumination windows 4A, 4B1, 4B2, 4C1, 4C2, 4D1 to 4D3, 4E1, 4E2 are not mutually distinguished.

Figure 3:
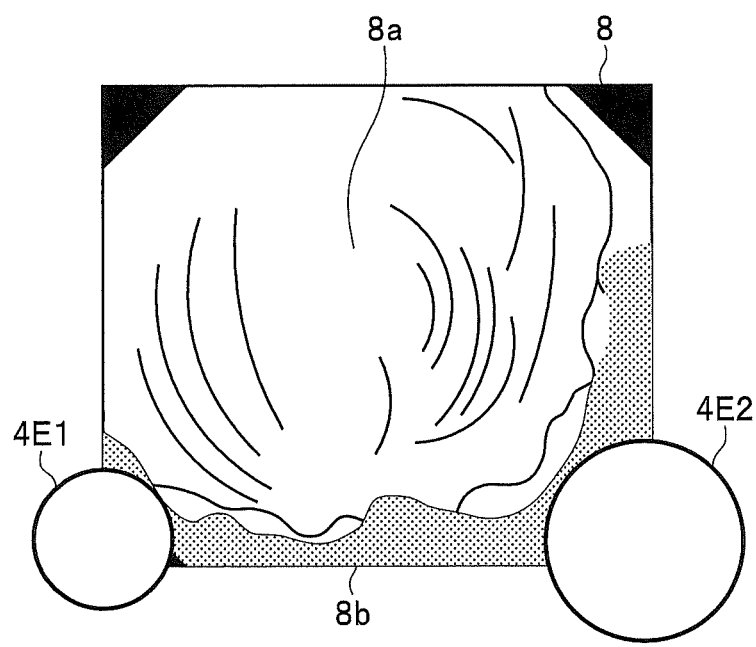
FIG. 3 is an explanatory diagram showing an example of a picked-up image when light adjustment control is performed without considering a distal end layout.

FIG. 3 is an explanatory diagram showing an example of a picked-up image when light adjustment control is performed without considering a distal end layout. The distal end layout shows a pattern of a distribution of illumination light emission positions relative to an arrangement of an image pickup device. In the light adjustment control without considering the distal end layout, the light adjustment control is performed based on brightness information obtained from the picked-up image.

In the light adjustment control, brightness to be targeted (a target value) is set. The target value is a reference value of brightness at the time of being displayed on a display and is set in advance. In the light adjustment control in an endoscope system, an amount of illumination light and the like are controlled, for example, so that an average brightness of a picked-up image corresponds to the target value.

FIG. 3 shows an example of a case where the E layout of FIG. 2E is adopted as a distal end layout of an endoscope insertion portion, and positions of the illumination windows 4E1 and 4E2 relative to an endoscopic image 8 are indicated by circle marks. The endoscopic image 8 of FIG. 3 is obtained by picking up an image of a predetermined lumen. A lumen part 8a is not sufficiently illuminated and is dark, and a biological tissue part 8b displayed on a lower side of the screen is illuminated by illumination light and is a bright image. In an E pattern, since the illumination windows 4E1 and 4E2 are arranged being biased on the lower side of the image pickup device 3E, the biological tissue part 8b displayed on the lower side of the screen is too bright, and halation is caused. Note that, in FIG. 3, it is shown by a dot pattern that the halation is caused.

Thus, in the present embodiment, the light adjustment control considering a distal end layout is performed to eliminate factors that hinder observation. For the control, information about the distal end layout, that is, light distribution information is stored in the endoscope memory.

In FIG. 1, an endoscope system 10 is configured with an endoscope 11, a video processor 21, a light source device 31 and a display device 41. The light source device 31 has a light source portion 32. The light source portion 32 is configured, for example, with an LED light source and is adapted to be capable of emitting illumination light according to an observation mode.

The endoscope 11 has an elongated insertion portion 12. On a distal end side of the insertion portion 12, an image pickup portion 13 having the image pickup device 3 such as a CCD or CMOS sensor is included. The insertion portion 12 is also provided with a light guide 14 for guiding illumination light from the light source device 31. A distal end of the light guide 14 is fitted to the illumination window 4 on a distal end face 12a of the insertion portion 12, and the light guide 14 is adapted to guide emitted light from the light source portion 32 of the light source device 31 to the distal end face 12a of the insertion portion 12 and causes the emitted light to be emitted from the illumination window 4.

Note that internal components for endoscope such as the treatment instrument channel in FIGS. 2A to 2E are not shown in FIG. 1. Further, though only one light guide is shown in FIG. 1, a plurality of illumination windows 4, which are emission ends of the light guide 14, may be provided by branching the light guide 14 as shown in FIGS. 2B to 2E.

Illumination light emitted from the illumination window 4 is radiated to a subject. Reflected light (return light) from the subject is incident on the image pickup device 3 via the observation window 2. The image pickup device 3 photoelectrically converts a subject optical image incident on the image pickup surface. The endoscope 11 is provided with an endoscope signal processing portion 15, and the image pickup portion 13 outputs an image pickup signal based on the subject optical image to the endoscope signal processing portion 15.

The endoscope signal processing portion 15 performs correction processing of scratches on the image pickup portion 13 for the image pickup signal from the image pickup portion 13. The endoscope signal processing portion 15 is adapted to, after amplifying the image pickup signal from which noise is removed, convert the image pickup signal to a digital signal by analog/digital conversion processing and output the digital signal to a video processing portion 22 of the video processor 21.

The video processor 21 is provided with a controlling portion 26 configured to control each portion. The controlling portion 26 may be configured with an FPGA (field programmable gate array) or may be configured with a processor such as a CPU and configured to control each portion according to a program stored in a memory not shown.

The video processing portion 22 performs various kinds of signal processing, such as color signal processing for generating a color signal, gamma correction processing, electronic zoom processing and white balance (W/B) processing, for the inputted image pickup signal, converts the image pickup signal to a display format suitable for the display device 41 and outputs the image pickup signal to the display device 41. In this way, an endoscopic image picked up by the image pickup portion 13 is displayed on a display screen of the display device 41.

In the present embodiment, the endoscope 11 is provided with an endoscope memory 16, and the endoscope memory 16 is adapted to store light distribution information. For example, the endoscope memory 16 may store information about a distal end layout as the light distribution information. Further, the endoscope memory 16 may be adapted to store an imager ID identifying the image pickup device 3. Further, the endoscope memory 16 may be adapted to, if a distal end layout type is already known as the distal layout information, store information showing a pattern type of the distal end layout. For example, the endoscope memory 16 may store information showing which of the A to E layouts the distal end layout is.

For example, when the number of distal end layout types is relatively small, for example, in the case of only the five types shown in FIGS. 2A to 2E, the endoscope memory 16 may be adapted to store the number of the illumination windows (the number of light guides) and an extension bit indicating whether or not an arrangement of the illumination windows is biased relative to an arrangement of the image pickup device 3, as the distal layout information. Note that not only whether or not the arrangement of the illumination windows is biased but also a direction of the bias may be shown by the extension bit.

For example, among the B, C and E layouts for which the number of the illumination windows is two, it is only the E layout that the arrangement of the illumination windows is biased relative to the arrangement of the image pickup device 3 in the vertical direction. Therefore, it is possible to distinguish the A layout, the B and C layouts, the D layout and the E layout from one another by the information about the number of the illumination windows and the extension bit for each of the layouts. Note that it is already known that, in the E layout, the illumination windows are arranged being biased in a screen downward direction relative to the image pickup device 3. In this case, the B and C layouts cannot be mutually distinguished. However, it does not matter in terms of the light adjustment control, because, in the B and C layouts, bias of the arrangements of the illumination windows relative to the image pickup device 3 is relatively small, and it is relatively rare that halation or the like occurs in a part of an image pickup image on the screen.

Note that the endoscope memory 16 may be adapted to store information obtained by determining a positional relationship between the observation window 2 and the image pickup device 3 by an angle and a distance, based on the screen upward direction, as the light distribution information.

Further, the endoscope memory 16 may be adapted to update the light distribution information by a setting operation by a user.

In the present embodiment, the video processor 21 has a parameter setting portion 24, and the parameter setting portion 24 is adapted to be capable of reading out the light distribution information stored in the endoscope memory 16.

The video processor 21 is also provided with a memory 25. The memory 25 stores information about a plurality of light adjustment parameters. Note that each light adjustment parameter is information including one or more parameters for the light adjustment control, and a plurality of such light adjustment parameters, each of which includes one or more parameters, are stored in the memory 25 according to pieces of the light distribution information.

For example, the memory 25 is caused to store the light adjustment parameters corresponding to the pieces of light distribution information in consideration of light adjustment states of existing endoscope models and light adjustment states based on simulation results. Note that information about the light adjustment parameters in the memory 25 may be configured to be updatable by an update operation by the user.

The parameter setting portion 24 is adapted to read out the information about the light adjustment parameters by referring to the memory 25 using the light distribution information read out from the endoscope memory 16, and set the light adjustment parameter for the video processing portion 22 and a light adjustment operating portion 23. Note that the parameter setting portion 24 may use both of the light distribution information and the imager ID to read out the light adjustment parameter from the memory 25.

Even when the information about the distal end layout is not stored in the endoscope memory 16 as the light distribution information, the parameter setting portion 24 may be adapted, by causing information for judging the information about the distal end layout stored in the memory 25, to judge the distal end layout based on the information read out from the endoscope memory 16 and, furthermore, to read out the light adjustment parameter based on a judgment result.

The light adjustment operating portion 23 as a light adjustment controlling portion is also given an endoscopic image (a picked-up image) from the video processing portion 22. The light adjustment operating portion 23 is adapted to calculate a detection value showing brightness of the endoscopic image using the light adjustment parameter. The light adjustment operating portion 23 generates a light adjustment control signal based on the calculated detection value and outputs the light adjustment control signal to a light source controlling portion 33. The light source controlling portion 33 is adapted to control an amount of illumination light to be an amount of light based on the light adjustment control signal by driving the light source portion 32 based on the light adjustment control signal.

Figure 4:
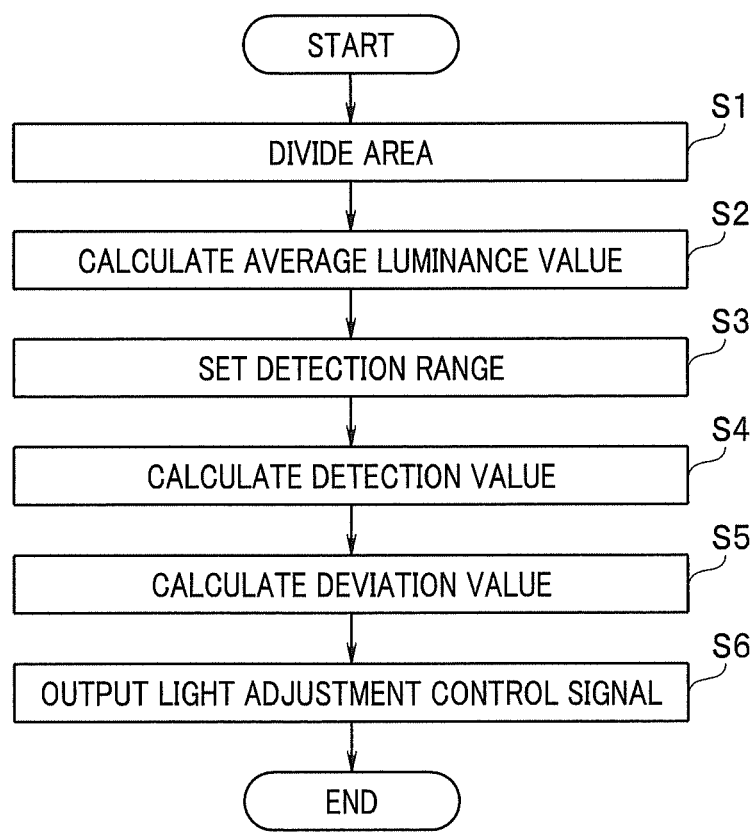
FIG. 4 is a flowchart showing an example of light adjustment control by a light adjustment operating portion 23.

FIG. 4 is a flowchart showing an example of the light adjustment control by the light adjustment operating portion 23.

The light adjustment operating portion 23 divides the picked-up image into predetermined small areas (step S1) and calculates an average luminance value for each of the small areas (step S2). Next, at step S3, the light adjustment operating portion 23 sets a predetermined area in a center of the picked-up image (hereinafter referred to as a detection range), and determines, for the detection range, a detection value based on the average luminance value of the each small area (step S4). At step S5, the light adjustment operating portion 23 determines the detection value/the target value as a deviation value (step S5) and outputs the deviation value to the light source controlling portion 33 as the light adjustment control signal (step S6).

The light source controlling portion 33 is adapted to control an amount of emitted light of the light source portion 32 so that the detection value/the target value are 1. In other words, the light source controlling portion 33 is adapted to increase the amount of emitted light to increase the detection value if the detection value is smaller than the target value, and decrease the amount of emitted light to decrease the detection value if the detection value is larger than the target value.

In the present embodiment, the detection range is adapted to be set by the light adjustment parameter. In other words, the detection range changes according to the distal end layouts. For example, the detection range by the light adjustment parameter based on the B layout is set in a center part of the screen, while the detection range by the light adjustment parameter based on the E layout is not only set in the center part of the screen but also spreads to a lower side of the screen.

FIG. 5 is an explanatory diagram for illustrating an example of a light adjustment parameter table stored in the memory 25. The example of FIG. 5 shows an example in which four kinds of image pickup devices Ty1 to Ty4 are adopted for endoscopes of the five distal end layout types of the A to E layouts shown in FIGS. 2A to 2E, as the image pickup device 3. It is shown that the image pickup device 3 of Ty1 is used for the endoscopes of the A, D and E layouts; the image pickup device 3 of Ty2 is used for the endoscopes of the B and D layouts; the image pickup device 3 of Ty3 is used for the endoscopes of the A, C and E layouts; and the image pickup device 3 of Ty4 is used for the endoscopes of the A, D and E layouts. Further, the example of FIG. 5 shows an example in which information about the number of the light guides (the number of LGs), which is the number of the observation windows, and the extension bit are stored in the endoscope memory 16. The example of FIG. 5 shows an example in which the light adjustment parameter is set based on only the information about the number of the light guides and the extension bit.

For example, the light adjustment parameter in a case where the number of light guides is one is a, and the light adjustment parameter in a case where the number of the light guides is three is c. When the number of the light guides is two, the light adjustment parameter in a case where the extension bit is 0 is b, and the light adjustment parameter in a case where the extension bit is 1 is b'. Note that each of the light adjustment parameters a, b, b' and c includes information about one or more parameters as described above.

In the example of FIG. 5, the light adjustment parameters b and c are for setting the predetermined range in the center of the screen as the detection range. The light adjustment parameter b' is for enlarging the detection range downward from the predetermined range in the center of the screen, and can suppress halation in a lower part of the screen. Note that the light adjustment parameter a is for enlarging the detection range upward from the predetermined range in the center of the screen, and can suppress halation in an upper part of the screen.

For example, in the example of FIG. 3, if the detection range by the light adjustment parameter b in the case where the number of the light guides is two (corresponding to the B layout) is adopted, the detection value is a small value because an average luminance value in the center part of the screen is relatively small, and the light source controlling portion 33 performs the light adjustment control so as to increase the amount of illumination light from the light source portion 32. As a result, halation is caused in the biological tissue part 8b in the lower part of the screen as described above. In comparison, in the present embodiment, the light adjustment parameter corresponding to the E layout is selected in the example of FIG. 3, and, thereby, the detection range spreads to the lower side of the screen. Therefore, in this case, the average luminance value of the biological tissue part 8b, which is relatively high, is used for calculation of the detection value, and the detection value is a relatively large value. Thus, the light source controlling portion 33 performs light adjustment control so as to decrease the amount of illumination light from the light source portion 32. As a result, halation in the biological tissue part 8b in the lower part of the screen is suppressed, and the biological tissue part 8b in the lower part of the screen can be an easy to see.

Note that the light adjustment control in FIG. 4 is an example, and the light adjustment operating portion 23 may calculate the light adjustment control signal by a method different from FIG. 4. For example, there is a method in which the average luminance values of the small areas are arrayed in descending order of magnitudes, and an average value of luminance values of a predetermined range of the array is set as a representative detection value of the predetermined range. By operation of representative detection values determined for a plurality of predetermined ranges, a detection value is calculated. In this case, by setting a weight for the each representative detection value based on a value of a predetermined high luminance value in a predetermined range including the center of the screen, the light adjustment control to suppress halation is possible. By setting the predetermined range including the center of the screen for which the value of the predetermined high luminance value is determined, by the light adjustment parameter based on the distal end layout, suitable light adjustment control according to the distal end layout is possible.

For example, as for the E layout, by setting a range including the lower part of the screen as the predetermined range including the center of the screen for which the value of the predetermined high luminance value is determined, it is possible to, by increasing the weight to the representative detection value of the relatively bright lower part of the screen, cause the detection value to be a relatively large value. Thus, it is possible to decrease the amount of illumination light from the light source portion 32 and suppress halation in the biological tissue part 8b in the lower part of the screen.

The light adjustment parameter setting example shown in FIG. 5 is an example. A different light adjustment parameter may be set for the each distal end layout, and the light adjustment parameter may be set in consideration of the type of the image pickup device.

Figure 6:
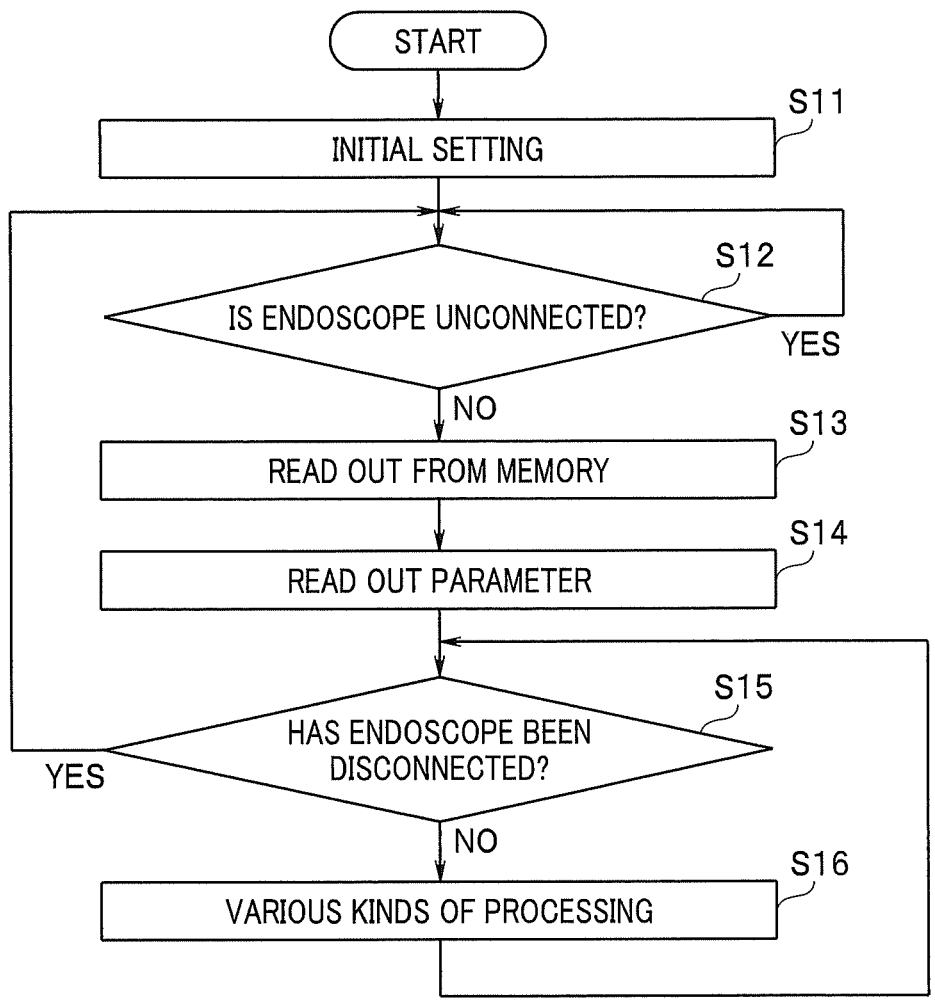
FIG. 6 is a flowchart for illustrating an operation of the first embodiment.
Figure 7:
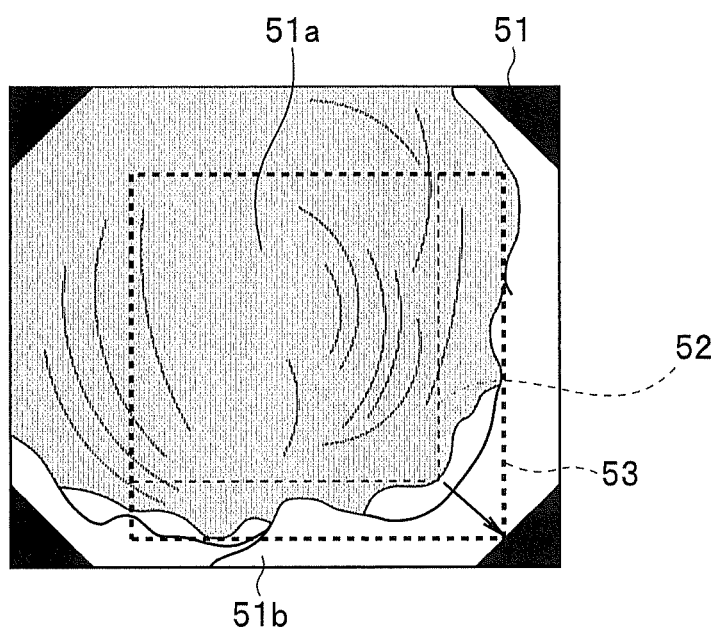
FIG. 7 is an explanatory diagram showing a picked-up image obtained when the light adjustment control in the first embodiment is adopted in the example of FIG. 3.
Figure 8:
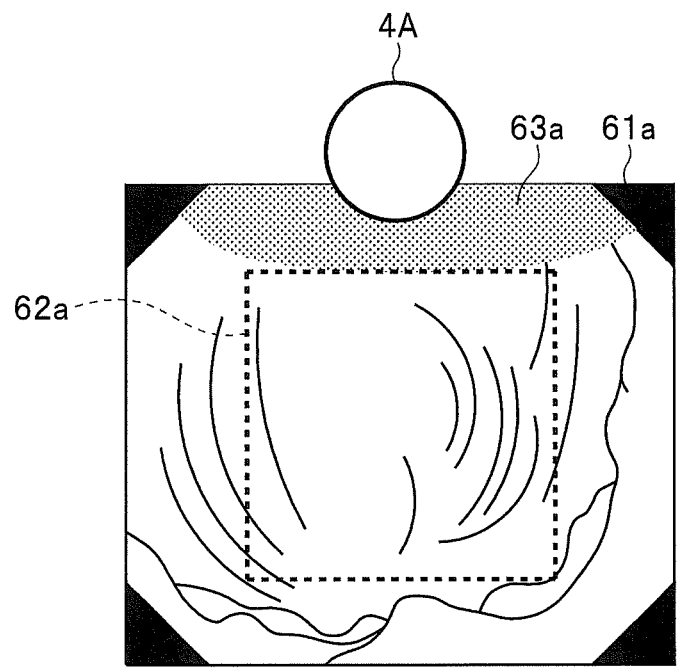
FIG. 8 is an explanatory diagram showing an example of a picked-up image when light adjustment control is performed in a state in which a predetermined range in a center of a screen is set as a detection range, in a case where an A layout is adopted.
Figure 9:
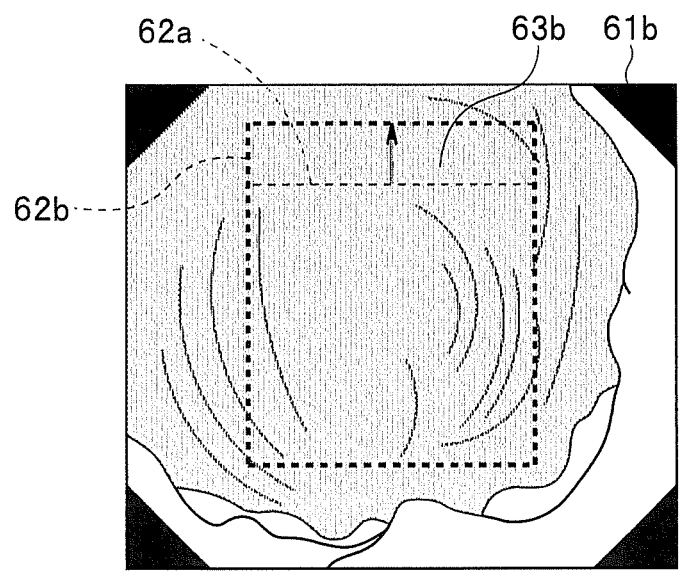
FIG. 9 is an explanatory diagram showing a picked-up image obtained when the light adjustment control in the first embodiment is adopted in the example of FIG. 8.

Next, an operation of the embodiment configured as described above will be described with reference to FIGS. 6 to 9. FIG. 6 is a flowchart for illustrating the operation of the first embodiment. FIG. 7 is an explanatory diagram showing a picked-up image obtained when the light adjustment control in the present embodiment is adopted in the example of FIG. 3. FIG. 8 is an explanatory diagram showing an example of a picked-up image when the light adjustment control is performed without considering the distal end layout, that is, in a state in which the predetermined range in the center of the screen is set as the detection range, in the case where the A layout is adopted. FIG. 9 is an explanatory diagram showing a picked-up image obtained when the light adjustment control in the present embodiment is adopted in the example of FIG. 8.

When power is turned on, the controlling portion 26 of the video processor 21 performs initial setting of each portion of the video processor 21 at step S11 in FIG. 6. Next, at step S12, the controlling portion 26 judges whether an endoscope is unconnected or not and enters a connection waiting state of waiting for connection of an endoscope. When the endoscope 11 is connected, the controlling portion 26 controls the parameter setting portion 24 to execute readout from the endoscope memory 16 at step S13. The light distribution information is stored in the endoscope memory 16, and the parameter setting portion 24 performs parameter setting for the light adjustment control based on the light distribution information by reading out the light distribution information from the endoscope memory 16.

In other words, the parameter setting portion 24 reads out the light adjustment parameter from the memory 25 using the read-out light distribution information. The light adjustment parameters corresponding to the pieces of light distribution information are stored in the memory 25, and the parameter setting portion 24 sets the light adjustment parameter corresponding to the light distribution information for the video processing portion 22 and the light adjustment operating portion 23.

The light distribution information is information about the distal end layout of the insertion portion 12, that is, the distribution of illumination light emission positions relative to the arrangement of the image pickup device 3. By setting the light adjustment parameter using the light distribution information, it is possible to perform suitable light adjustment control at a predetermined position on the screen.

FIG. 7 shows a picked-up image 51 obtained when the E layout of FIG. 2E is adopted as the distal end layout. Both of FIGS. 3 and 7 show picked-up images in the same photographing range that have been picked up by same-type image pickup devices of endoscopes adopting the same E layout. FIG. 3 shows an example in which the light adjustment control has been performed, with an area 52 in the center of the screen in FIG. 7 as a detection range. In comparison, FIG. 7 shows that the light adjustment control has been performed, with an area 53 spreading downward of the screen and to a right side of the screen more than the area 52, as a detection range as indicated by an arrow.

As shown in FIG. 3, in the E layout, the illumination windows 4E2 and 4E1 are located at lower right and lower left positions relative to the arrangement of the image pickup device 3, that is, relative to a position of the screen obtained by the image pickup device 3. The illumination window 4E2 is larger than the illumination window 4E1 in size. Therefore, by using a parameter for setting the detection range considering the distribution of the illumination light emission positions of the illumination windows 4E2 and 4E1 relative to the arrangement of the image pickup device 3, as the light adjustment parameter corresponding to the E layout, it is possible to suppress halation in the lower part of and on the right side of the screen.

For example, in the case of performing near-point observation of a biological tissue of a lumen as in FIG. 7, observation with the biological tissue, which is a target to be observed, located on the lower side of the screen is often performed. Therefore, when an endoscope of the E layout is adopted, it is more possible to suppress halation on the lower side of the screen by expanding the detection range to the lower side of the screen to determine the detection value for the light adjustment control.

As a result of such light adjustment control, a biological tissue part 51b on the lower side of the screen is an image easy to see, in which halation is suppressed, though a lumen part 51a in the center of the screen is relatively dark in FIG. 7.

FIGS. 8 and 9 show picked-up images 61a and 61b obtained when the A layout of FIG. 2A is adopted as the distal end layout. Both of FIGS. 8 and 9 show picked-up images in the same photographing range that have been picked up by the same-type image pickup devices of endoscopes adopting the same A layout. FIG. 8 shows an example in which, without adopting the light adjustment control of the present embodiment, light adjustment control has been performed with an area 62a in the center of the screen as a detection range. In comparison, FIG. 9 shows that, by adopting the light adjustment control of the present embodiment and selecting the light adjustment parameter corresponding to the distal end layout, the light adjustment control has been performed, with an area 62b spreading upward of the screen more than the area 62a as the detection range as indicated by an arrow.

As shown in FIG. 8, in the A layout, the illumination window 4A is located at an upper end position from the center in the horizontal direction relative to the arrangement of the image pickup device, that is, relative to a position of the screen obtained by the image pickup device. It is shown that, as a result, the amount of illumination light increases due to the detection value for which the average luminance value of the lumen part in the relatively dark center of the image is used and halation (a dot pattern part) is caused in the biological tissue part 63a in the upper part of the screen.

In comparison, in the present embodiment, a parameter for making a setting to expand the detection range upward in consideration of the distribution of the illumination window 4A relative to the arrangement of the image pickup device is used as the light adjustment parameter corresponding to the A layout. As a result, the detection value is a relatively large value; the amount of illumination light decreases; occurrence of halation in the biological tissue part 63b in the upper part of the screen is suppressed; and an image easy to see is obtained.

The controlling portion 26 judges at step S15 whether the endoscope has been disconnected or not, and executes various kinds of processing at step S16 until the endoscope is disconnected. When the endoscope is disconnected, the controlling portion 26 returns the process to step S12 and enters the endoscope connection waiting state.

As described above, in the present embodiment, the light distribution information, for example, the distal end layout is caused to be stored in the endoscope memory, and the light distribution information is read out from the endoscope to set the light adjustment parameter based on the read-out light distribution information. The light distribution information shows a relationship between the arrangement of the image pickup device and the distribution of the illumination light emission positions. By setting the light adjustment parameter using the light distribution information, it becomes possible to optimize brightness at a predetermined position on the screen and obtain the endoscopic image that is easy to observe.

(Modification)

FIG. 10 is an explanatory diagram for illustrating a modification. FIG. 10 is for describing information stored in the memory 25. In FIG. 4, an example of setting the light adjustment parameter based on the imager ID and the light distribution information has been described. In the present modification, setting of the light adjustment parameter is changed not only according to the imager ID and the light distribution information but also according to the observation site.

As shown in FIG. 10, the memory 25 stores a table in which the light adjustment parameter is set based on the observation site and the distal end layout, that is, the number of the light guides (the number of LGs) and the extension bit. Note that each of the light adjustment parameters P1 to P9 in FIG. 10 includes information about one or more parameters.

In the present modification, not only the light distribution information but also information about the observation site is stored in the endoscope memory 16. The parameter setting portion 24 is adapted to acquire the light distribution information and the information about the observation site from the endoscope memory 16 and select the light adjustment parameter corresponding to the light distribution information and the information about the observation site from the memory 25.

In the example of FIG. 10, for example, even in the case of the D layout for which the number of the light guides is three, the light adjustment parameter P5 is selected if the observation site is an upper digestive tract, and the light adjustment parameter P8 is selected if the observation site is a lower digestive tract. For example, as for the B and C layouts for which the number of the light guides is two, the light adjustment parameter P2 is selected if the observation site is a bronchus, the light adjustment parameter P3 is selected if the observation site is an upper digestive tract, the light adjustment parameter P6 is selected if the observation site is a lower digestive tract, and the light adjustment parameter P9 is selected if the observation site is a trans-nasally observed site.

For example, as for the E layout for which the number of the light guides is two, and the extension bit is 1, the light adjustment parameter P4 is selected if the observation site is the upper digestive tract, and the light adjustment parameter P7 is selected if the observation site is the lower digestive tract.

Note that, similarly to FIG. 4, the light adjustment parameter P1 selected for the A layout is set as a parameter to suppress halation in the upper part of the screen, and the light adjustment parameters P4 and P7 selected for the E layout are set as parameters to suppress halation in the lower part of the screen.

Other components, operations and effects are similar to the components, operation and effects of the first embodiment.

Second Embodiment

Figure 11:
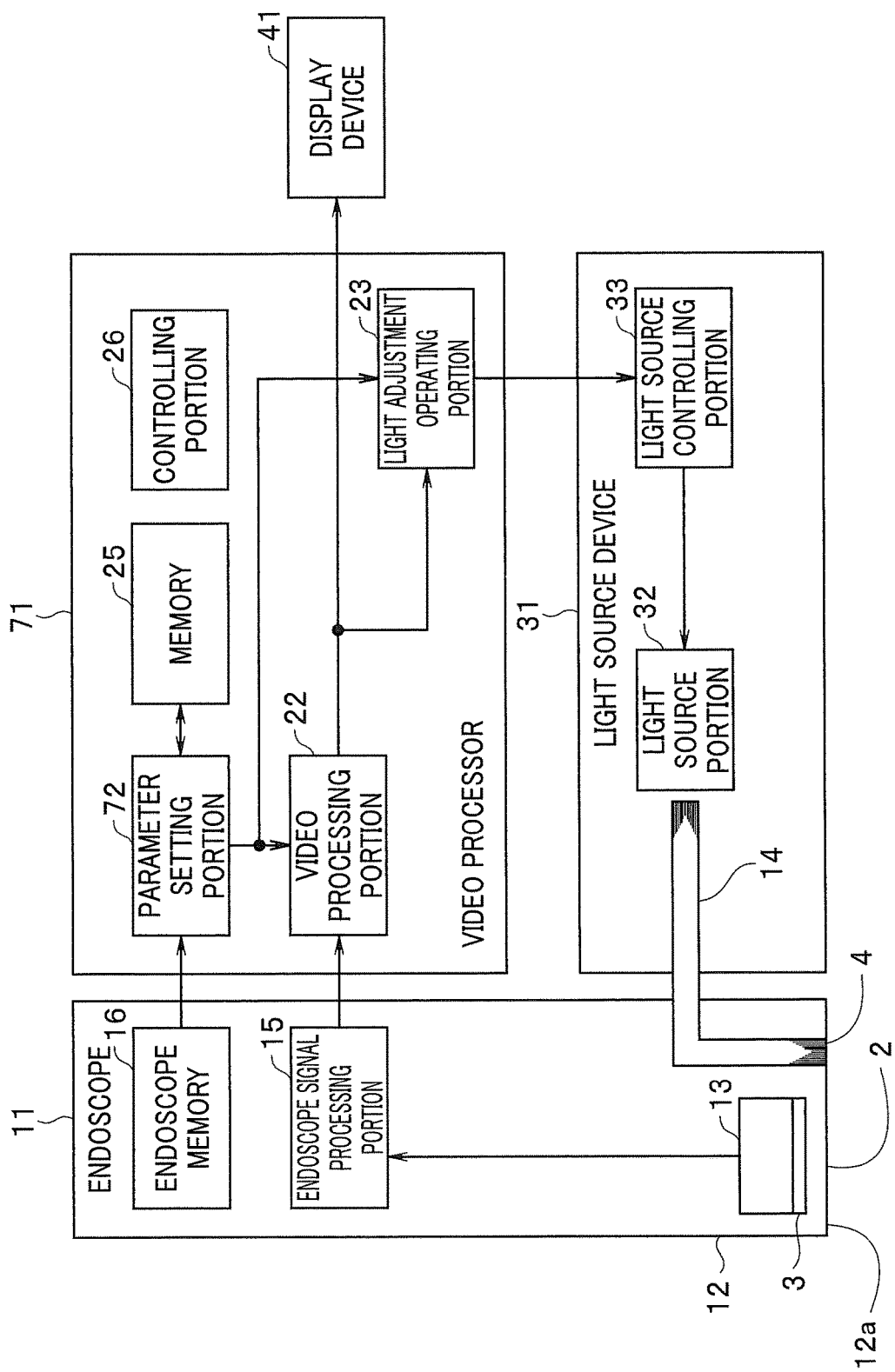
FIG. 11 is a block diagram showing a second embodiment of the present invention.

FIG. 11 is a block diagram showing a second embodiment of the present invention. In FIG. 11, the same components as FIG. 1 are given the same reference numerals, and description of the components will be omitted. The present embodiment is different from the first embodiment in that a video processor 71 adopting a parameter setting portion 72 is used instead of the parameter setting portion 24.

In the first embodiment, the endoscope memory 16 is caused to store the light distribution information; the memory 25 is caused to store the plurality of light adjustment parameters; and the light adjustment parameter is selected based on the light distribution information. In comparison, in the present embodiment, the endoscope memory 16 is adapted to store not only the light distribution information but also a part of the light adjustment parameters and a parameter flag specifying that the parameter is to be used. Note that the light adjustment parameter stored in the endoscope memory 16 corresponds at least to the light distribution information such as the distal end layout of the endoscope 11. As the light adjustment parameter stored in the endoscope memory 16, parameters corresponding to the imager ID and the observation site may be also stored in addition to the light distribution information.

The parameter setting portion 72 reads out the light distribution information stored in the endoscope memory 16 and reads out the parameter flag. The parameter setting portion 72 is adapted to, if it is specified by the parameter flag to use the light adjustment parameter in the endoscope memory 16, read out the specified light adjustment parameter and stores the light adjustment parameter into the memory 25.

The parameter setting portion 72 is adapted to preferentially use the light adjustment parameter read out from the endoscope memory 16 and select the light adjustment parameter stored in the memory 25 based on the read-out light distribution information.

Figure 12:
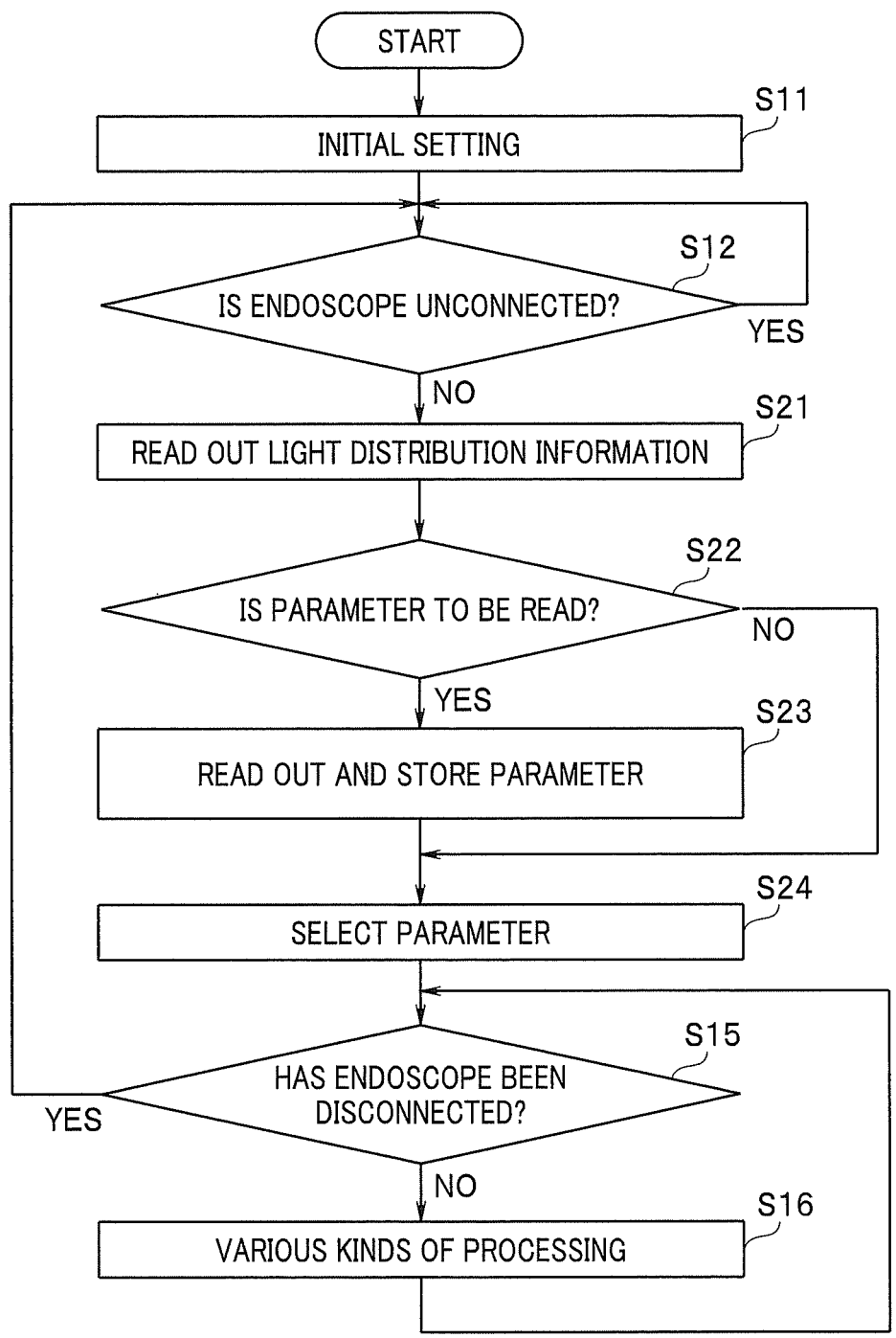
FIG. 12 is a flowchart for illustrating an operation of the second embodiment.

Next, an operation of the embodiment configured as described above will be described with reference to FIG. 12. FIG. 12 is a flowchart for illustrating the operation of the second embodiment. In FIG. 12, the same procedures as FIG. 6 are given the same reference numerals, and description of the procedures will be omitted.

At step S21 in FIG. 12, the parameter setting portion 72 reads out the light distribution information from the endoscope memory 16. At step S22, the parameter setting portion 72 verifies the parameter flag and judges whether use of the light adjustment parameter stored in the endoscope memory 16 is specified or not. If it is specified to read out the parameter, the parameter setting portion 72 reads out the specified parameter, gives the parameter to the memory 25 to cause the memory 25 to store the parameter, at step S23. Note that, if it is not specified to read out the parameter, the parameter setting portion 72 causes the process to transition from step S22 to step S24.

At step S24, the parameter setting portion 72 refers to the memory 25 based on the light distribution information to select and read out the light adjustment parameter. In this case, the parameter setting portion 72 performs the selection of the light adjustment parameter in a manner of preferentially using the light adjustment parameter read out from the endoscope memory 16. The parameter setting portion 72 outputs the light adjustment parameter to the video processing portion 22 and the light adjustment operating portion 23.

Other operations are similar to the operations of the first embodiment.

Thus, in the present embodiment, effects similar to the effects of the first embodiments are obtained, and it is possible to, by storing the light adjustment parameter in the endoscope memory 16, perform the light adjustment control using the light adjustment parameter stored in the endoscope memory 16 even in the case of the light adjustment parameter or image pickup device of a type that is not registered with the memory 25 of the video processor 71.

The present invention is not limited to each of the above embodiments as it is, but can be embodied by modifying the components within a range not departing from the gist of the invention at an implementation stage. Further, various kinds of inventions can be formed by appropriately combining a plurality of components disclosed in each of the above embodiments. For example, some components among all the components shown in each embodiment may be deleted. Furthermore, components between the different embodiments may be appropriately combined.

What is claimed is:

1. An endoscope system comprising: an endoscope including an image pickup sensor configured to pick up an image of an inside of a subject and one or more illuminating windows configured to emit illumination light; and a processor, the endoscope system configured to select a light adjustment parameter used for light adjustment control of the illuminating windows from among a plurality of light adjustment parameters each of which includes one or more parameters about light adjustment, based on light distribution information which is information indicating a relationship between an arrangement of the image pickup sensor and a distribution of illumination light emission positions corresponding to positions of the illuminating windows and which includes information about a light distribution angle of the illumination light and a number of the illuminating windows, to perform light adjustment control, wherein
the endoscope includes an endoscope memory configured to store the light distribution information, a part of parameters of the light adjustment parameter, and a parameter flag specifying that the part of the parameters are used for the light adjustment;
the processor includes a memory configured to store the plurality of light adjustment parameters corresponding to pieces of the light distribution information according to a plurality of types of endoscopes; and
the processor reads out the light distribution information, the part of the parameters, and the parameter flag from the endoscope memory, and controls amounts of light of the illuminating windows by selecting the part of the parameters with priority over the light adjustment parameters stored in the memory at time of selecting the light adjustment parameter based on the light distribution information, if it is specified by the parameter flag that the part of the parameters are used for the light adjustment.

2. The endoscope system according to claim 1, wherein the light distribution information includes distal end layout information indicating a layout of an arrangement position of the image pickup sensor and the illumination light emission positions.

3. The endoscope system according to claim 1, wherein the light distribution information includes a number of the illumination light emission positions and extension information indicating whether or not the illumination light emission positions are biased relative to the arrangement position of the image pickup sensor.

4. The endoscope system according to claim 1, wherein
the endoscope memory stores observation site information; and
the processor reads out the light adjustment parameter based on the light distribution information and the observation site information.

5. The endoscope system according to claim 1, wherein
the endoscope memory stores an imager ID; and
the processor reads out the light adjustment parameter based on the light distribution information and the imager ID.

6. The endoscope system according to claim 1, wherein the processor specifies a detection range used for the light adjustment control based on the light adjustment parameter.

7. The endoscope system according to claim 1, wherein the processor is connectable to another endoscope different from the endoscope, the other endoscope including an image pickup sensor configured to pick up an image of an inside of a subject, illuminating windows configured to emit illumination light, and an endoscope memory configured to store the light distribution information for illumination control of the other endoscope, the part of the parameters and the parameter flag; and
based on the light distribution information, the part of the parameters and the parameter flag read out from the endoscope or the other endoscope connected to the processor, the processor controls the amounts of light of the illuminating windows of the endoscope or the other endoscope that is connected.

8. A processor connectable to an endoscope including an image pickup sensor configured to pick up an image of an inside of a subject and one or more illuminating windows configured to emit illumination light, the processor configured to select a light adjustment parameter used for light adjustment control of the illuminating windows from among a plurality of light adjustment parameters each of which includes one or more parameters about light adjustment, based on light distribution information which is information indicating a relationship between an arrangement of the image pickup sensor and a distribution of illumination light emission positions corresponding to positions of the illuminating windows and which includes information about a light distribution angle of the illumination light and a number of the illuminating windows, to perform light adjustment control, wherein
the processor includes a memory configured to store the plurality of light adjustment parameters corresponding to pieces of the light distribution information according to a plurality of types of endoscopes; and
the processor reads out the light distribution information, a part of the parameters, and a parameter flag specifying that the part of the parameters are used for the light adjustment that are stored in the endoscope that is connected, and controls amounts of light of the illuminating windows by selecting the part of the parameters with priority over the light adjustment parameters stored in the memory at time of selecting the light adjustment parameter based on the light distribution information, if it is specified by the parameter flag that the part of the parameters are used for the light adjustment.

* * * * *